(12) United States Patent
Herder et al.

(10) Patent No.: US 8,051,851 B2
(45) Date of Patent: Nov. 8, 2011

(54) INHALER FOR THE ADMINISTRATION OF POWDERED PHARMACEUTICALS, AND A POWDER CARTRIDGE SYSTEM FOR USE WITH THIS INHALER

(75) Inventors: Martin Herder, Rodgau (DE); Ingo Mett, Frankfurt (DE); Joachim Goede, Hanau (DE)

(73) Assignee: Sofotec GmbH & Co. KG, Bad Homburg (DE)

( * ) Notice: Subject to any disclaimer, the term of this patent is extended or adjusted under 35 U.S.C. 154(b) by 643 days.

(21) Appl. No.: 11/183,182

(22) Filed: Jul. 18, 2005

(65) Prior Publication Data

US 2006/0037612 A1 Feb. 23, 2006

Related U.S. Application Data

(60) Provisional application No. 60/588,382, filed on Jul. 16, 2004.

(51) Int. Cl.
*A61M 15/00* (2006.01)
*A61M 11/00* (2006.01)
*A61M 15/08* (2006.01)
*A61M 15/06* (2006.01)

(52) U.S. Cl. ......... 128/203.12; 128/203.15; 128/200.23; 128/200.24; 128/203.19; 128/203.21; 128/203.23; 128/202.21

(58) Field of Classification Search ............. 128/203.12, 128/203.15, 200.23, 200.24, 203.19, 203.21, 128/203.23, 202.21
See application file for complete search history.

(56) References Cited

U.S. PATENT DOCUMENTS

| | | |
|---|---|---|
| 2,587,215 A | 2/1952 | Priestly |
| 4,274,403 A | 6/1981 | Struve |
| 4,668,218 A | 5/1987 | Virtanen et al. |
| 5,263,475 A | 11/1993 | Altermatt et al. |
| 5,301,666 A | 4/1994 | Lerk et al. |
| 5,320,714 A | 6/1994 | Brendel et al. |
| 5,435,301 A | 7/1995 | Herold et al. |
| 5,437,270 A | 8/1995 | Braithwaite et al. |
| 5,505,198 A | 4/1996 | Siebens et al. |
| 5,544,647 A | 8/1996 | Jewett et al. |
| 5,840,279 A | 11/1998 | Narodylo et al. |
| 6,071,498 A | 6/2000 | Narodylo et al. |
| 6,240,918 B1* | 6/2001 | Ambrosio et al. ....... 128/203.15 |

FOREIGN PATENT DOCUMENTS

CA    2 090 227 C    3/1992
(Continued)

*Primary Examiner* — Patricia Bianco
*Assistant Examiner* — Nihir Patel
(74) *Attorney, Agent, or Firm* — Venable LLP; Zayd Alathari (57) ABSTRACT

In order to improve the security and reliability of administration of powdered pharmaceuticals through dry powder inhalers, the invention proposes an inhaler (1) for powdered medicaments, comprising an activating device (4) for manual engagement by the patient for repeatedly metering a dose of medicament to be administered to the patient, and further comprising an advancing mechanism (25) for advancing a counter or indexing means (8) each time the activating device (4) has been engaged by the patient so that a dose of medicament has been released for administration to the patient, wherein the counter or indexing means (8) comprises an index (9), the index (9) being detectable by a detection means (10) of the inhaler, and the detection means (10) being coupled to a locking mechanism (12), the locking mechanism (12) blocking the activating device (4) and/or any transportation mechanism (5) of the inhaler (1) delayed by a predetermined number of metering cycles since detection of the index (9), and a cartridge (3).

17 Claims, 8 Drawing Sheets

FOREIGN PATENT DOCUMENTS

| | | |
|---|---|---|
| DE | 846 770 | 8/1952 |
| DE | 35 35 561 C2 | 5/1986 |
| DE | 44 00 083 C2 | 7/1995 |
| DE | 44 00 084 A1 | 7/1995 |
| DE | 195 23 516 C1 | 10/1996 |
| DE | 195 22 415 A1 | 1/1997 |
| DE | 195 22 416 A1 | 1/1997 |
| EP | 0 416 950 A1 | 3/1991 |
| EP | 0 416 951 A1 | 3/1991 |
| EP | 0 640 354 A2 | 3/1995 |
| EP | 0 837 710 B1 | 4/1998 |
| GB | 2 165 159 A | 4/1986 |
| NZ | 310990 A | 3/2000 |
| WO | WO-92/00771 | 1/1992 |
| WO | WO-92/09322 | 6/1992 |
| WO | WO-93/11773 | 6/1993 |
| WO | WO-93/16748 | 9/1993 |
| WO | WO-94/14492 | 7/1994 |
| WO | WO-95/31237 | 11/1995 |
| WO | WO-97/00703 A1 | 1/1997 |
| WO | WO 00/59806 | 10/2000 |
| WO | WO-00/74754 | 12/2000 |
| WO | WO-02/24268 A1 | 3/2002 |
| WO | WO-02/24269 A1 | 3/2002 |
| WO | WO 2004/026380 | 4/2004 |

* cited by examiner

Fig. 19 under the assumption of more or less empty storage space. An inhaler with an integrated counting mechanism by a toothed wheel in connection with an actuation button is disclosed in WO 98/28033, corresponding to U.S. Pat. No. 6,328,037. An inhaler with two integrated displays is disclosed in U.S. Pat. No. 4,984,158 and another with a counting wheel with a numerical display in WO 98/56444. More developed counting mechanisms are disclosed in WO 03/020349, and in WO 03/063754 A1 and WO 03/063754 A2, both corresponding to U.S. Pat. No. 6,752,153 B1, in which numbers of actuations of an inhaler are counted and displayed in a window.

INHALER FOR THE ADMINISTRATION OF POWDERED PHARMACEUTICALS, AND A POWDER CARTRIDGE SYSTEM FOR USE WITH THIS INHALER

FIELD OF THE INVENTION

The invention relates to an Inhaler for the administration of powdered pharmaceuticals, and a powder cartridge for powdered pharmaceuticals for use with this inhaler, particularly to a multi dose dry powder inhaler with a dosing counting or indexing means provided in the inhaler or the cartridge.

BACKGROUND OF THE INVENTION

In the field of treatment of bronchial diseases, and also of other diseases in which medication can be given via the airways, it is known not only to atomize liquid solutions or suspensions into inhalable aerosols but also to administer powdered medicaments. Many examples of such medicaments are described in the literature, and of these we refer purely by way of illustration to WO 93/11773, EP 0 416 950 A1 and EP 0 416 951 A1.

A customary form of administration in this regard is the delivery via an inhalation device, a so-called inhaler. Known inhalers for powdered pharmaceuticals include those for administration of a single dose and also inhalation devices which have one or more reservoirs for a plurality of pharmaceutical doses. In this connection, it is known either to provide separate storage spaces for each individual dose or to provide one single reservoir space for receiving a multiplicity of doses of a medicament during the manufacturing process.

Known inhalers in which a multiplicity of individual doses are provided in separate storage spaces include those in which individual areas of the inhaler are each filled with a pharmaceutical dose. An example of such an inhaler is described in U.S. Pat. No. 5,301,666. However, it is also known to accommodate a multiplicity of pharmaceutical powder doses in separate areas, so-called blister packs. An example of such a blister pack for use with an inhaler is described in DE 44 00 083 C2. A similar blister pack which is designed integral with a disposable inhaler is described for example in DE 44 00 084 A1. An inhalation device into which blister packs can be inserted, which each have separate storage spaces for individual doses of a powdered pharmaceutical and which can be emptied one after another with the aid of the inhalation device, is described, for example, in DE 195 23 516 C1. Typically, the number of remaining doses is easily assessable for the patient using the inhaler. The blister cavities already emptied and those still containing an available dose of medicament powder can easily be recognized, as the emptied ones are usually destroyed while releasing the medicament dose. Further, such kinds of blister packs are typically formed from a transparent film on one side, thus allowing visual inspection of the number of doses remaining available.

Many examples of inhalers with a storage space for a multiplicity of pharmaceutical doses are described in the prior art. One example with an exchangeable storage container is described in German Patent Specification 846 770, and another in WO 95/31237. An important problem with inhalation systems in which a multiplicity of doses of a medically active substance are accommodated in a common storage space concerns the apportioning of an individual dose for one individual inhalation. A great many solutions have been proposed to solve this problem, for example those which are described in U.S. Pat. No. 2,587,215 and U.S. Pat. No. 4,274,403. Other types of arrangements for metering an individual dose of pharmaceutical powder from a storage space for a multiplicity of pharmaceutical doses are described in WO 92/09322, WO 93/16748 and DE 35 35 561 C2 and in GB 2 165 159 A. An exchangeable cartridge for receiving a multiplicity of doses of a pharmaceutical powder with an integrated metering slide is known from DE 195 22 415 A1.

Another important problem with inhalation of pharmaceutical powders concerns the breakdown of the galenic powder formulations into particles which can access the lungs. The active substances administered in this way are generally combined with vehicles in order to achieve a reasonable dosing capacity of the medically active substance and to set further properties of the pharmaceutical powder, which for example can influence the storage life.

Proposed solutions concerning the designs of powder inhalers with which particles which can access the lungs are intended to be made available in an air stream for inhalation are described for example in EP 0 640 354 A2, U.S. Pat. No. 5,505,196, U.S. Pat. No. 5,320,714, U.S. Pat. No. 5,435,301, U.S. Pat. No. 5,301,666, DE 195 22 416 A1 and WO 97/00703. Proposals are also known to use auxiliary energy to generate the air stream, for example from ZA-A 916741.

In the use of medicaments for inhalation in powder form, it is also quite generally known to combine active substances by administering prepared active substance mixtures. Corresponding proposals are found in EP 0 416 951 A1 and WO 93/11773, for example for combination of salmeterol and fluticasone or formoterol and budesonide.

WO 00/74754 and many other publications over a period of more than twenty years have described how, particularly in powder inhalers, there is a considerable problem with moisture. Not only can moisture have a disadvantageous effect on the pharmaceutically active composition of the medicament, it can also impair in particular the interplay of physical and chemical parameters of the combination of active substance and auxiliaries. As a result, lumps may form, for example, or the breakdown of the inhaled powder into particles which can access the lungs may be impaired. All these circumstances can lead to problems affecting the metering and the efficacy of the administration of a powdered medicament.

To minimize these disadvantages, various attempts have already been made in the past to reduce the penetration of moisture into a powder inhaler by using seals. Attempts have also been made to reduce the disadvantageous effects of penetrated moisture by providing desiccants to absorb the moisture, in particular to keep the air moisture in storage chambers to a minimum.

Various attempts have been made to improve dry powder inhalers with respect to the reliability and applicability of dry powder inhalation and cost effective medical treatment particularly for long term application of medicaments.

PRIOR ART

With respect to multiple dose inhalers, also various attempts have been made to include various kinds of counting or indexing means to show a number of actuations of an inhaler to the user. U.S. Pat. No. 4,668,218 A discloses a disc type inhaler with a toothed wheel with color markings, which is in gear engagement with the disc of the inhaler, and thus urged to rotate according to the rotation of the disc. So, the toothed wheel with markings may show a marking depending on the number of rotations of the disc. WO 92/00771, corresponding to U.S. Pat. No. 5,437,270, discloses an inhaler with an integrated storage chamber for a multiplicity of medicament doses. After removing the number of doses provided in the chamber the inhaler is normally intended to be disposed of. Further described is a display means for counting the number of times the inhaler has been actuated. Whilst actuating a button a gear mechanism rotates a drum, onto which a tape having markings thereon is wound, thereby routing the tape through a window presenting the markings to the user. The markings in fact indicate the number of actuating actions performed, however, it is intended to provide an estimation of a number of medicament doses removed from or remaining in the storage chamber. WO 94/14492 discloses an inhaler for providing a number of medicament doses. After removing the number of doses provided from the inhaler it is intended to be disposed of. Further it is described a display means for counting the number of actuations or doses. Further, an electronic counter is disclosed as an embodiment of the invention, which further increases the costs for use of such an inhaler as well as additional costs for recycling or disposal of electronic apparatus waste.

From U.S. Pat. No. 5,840,279 A, WO 97/00703 A1, and DE 195 22 415 A1 a replaceable powder cartridge is known having a counting means and a display means showing the number of doses remaining available in the cartridge, or the number of doses removed from said cartridge. Although there is visual information available, for a patient using an inhaler with such a cartridge inserted, that there is little or no medicament available, one could further actuate the dosing mechanism of such an inhaler and seek to obtain to remove the very remainder of the medicament powder comprised in the cartridge.

Contrary to common aerosol inhalers, multi dose dry powder inhalers do generally not suffer from a variation of the content of the medically active components of the composition in the doses provided when the inhaler is close to empty state. However, the accuracy of a metered dose typically decreases, and, even more dangerous for the patient, he may actuate and use the inhaler without getting any medically active substance from an empty inhaler at all, thus causing risk of life for certain diseases treated with dry powder inhalation by not receiving the required medicament dose.

WO 02/24268 A1 discloses a reusable inhaler for use with exchangeable cassettes, each containing a predetermined number of separately stored pre-metered doses. The inhaler described comprises a dose counter and a cassette counter. The invention as disclosed is based on the general statement that it would be generally undesirable to have a multiplicity of medicament doses stored within a single storage space. The cassette, being an exchangeable dose member, carries a number of sequentially accessible individually sealed pre-metered doses. The sealing of each dose should ensure a sufficiently stable storing of the medicament powder during the lifetime of such a dosing cassette. The inhaler disclosed has a quite complicated spring loaded mechanism to perform the steps of cutting the sealing, triggering and moving the cassette along a fixed suction tube of a mouthpiece and braking the cassette during motion to control the time it takes for the cassette to pass the suction tube, thus controlling the time during which medicament powder is available for inhaling by the patient. Activation and locking of the inhaler is performed by pulling a covering lid and pushing it to a closing position. Before the first dose of medicament can be delivered a cassette which comes in a box has to be inserted into the inhaler together with that box. Then the inhaler must first be opened by pulling the lid and shut again. In this way a mechanism extracts the cassette from the protective box and brought into a loaded position, whilst, at the same time a cassette drive spring is tensioned and secured by a plunger element.

After an inhalation cycle, a revolver mechanism moves the cassette so that a fresh sealed dose is exposed to the cutter mechanism for the next inhalation cycle. Opening the inhaler reveals a removable mouthpiece.

WO 02/24269 A1 likewise discloses such kind of inhaler. More specifically, the dose counter and the cassette counter of WO 02/24268 A1 are described in more detail. As it is evident from the design principle, the number of doses obtainable from a single cassette is quite limited compared to a pharmaceutical powder cartridge as known from U.S. Pat. No. 5,840, 279 A and WO 97/00703 A1. The dose counter as disclosed is for a one digit number of doses, the embodiment described shows a count down starting at seven doses per cassette. The dose counter mechanism is located in the inhaler and not inside the cassette. Once the dose counter is down to zero, a mechanism returns the cassette to the storage box and the plunger and catching mechanism releases the box so that it can be removed by the user and replaced by a new one. However, there is no disclosure how such a mechanism should function or look like.

There is a second counter disclosed, being described as a cassette counter which counts down the number of cassettes used with the inhaler. The counter display can be seen from the outside of the inhaler and the embodiment described shows a count down starting at fifty-cassettes before the inhaler is considered being worn out. When such cassette counter is down to zero, the cassette will not be released as described above, but the inhaler cannot be used any more and has to be discarded. Again, there is no disclosure how such a mechanism should function or look like. Besides, the cassette counter is described to comprise a visual indication, e.g. an inverted prompt of the number shown, to remind the user to exchange the mouthpiece of the inhaler, which is described as being required for reasons of hygiene, maybe due to the fact that the suction tube of the mouthpiece is being described as porous (WO 02/24268 A1). The typical exchange interval for the mouthpiece is indicated as with every fifth cassette, that is typically after 35 doses have been obtained from the inhaler.

Thus, the typical number of total doses which can be obtained from such inhaler is 350 medicament doses, which seems to be reasonable considering the wear and tear of the obviously complicated mechanisms required caused by the abrasive properties and possible agglomerations of the medicament powder. This is a quite short lifetime of the inhaler compared to the inhaler known from U.S. Pat. No. 5,840,279 A, and WO 97/00703 A1. Generally, the inhaler disclosed in WO 02/24269 A1 and WO 02/24268 A1 lacks from the same disadvantages as other inhalers do designed for administration of medicament doses from individually sealed single dose compartments, a number of which is arranged on a common carrier, like a blister pack, as discussed above with respect to DE 195 23 516 C1, for instance. More particularly, the use of the inhaler suggested in WO 02/24269 A1 and WO 02/24268 A1 seems to be extremely costly, both due to single dose packaging as well as discarding a lot of inhaler parts and boxes, as well as the inhaler itself, after a relatively small number of administered doses.

The object of the invention is therefore to improve known systems for administration of powdered pharmaceuticals.

SUMMARY OF THE INVENTION

According to the invention, this object is achieved by an inhaler for powdered medicaments, for providing a large number of doses of pharmaceutical powder medicament from a single reservoir space or a multiplicity of reservoir spaces, which medicament can be received by a patient by means of an air stream, the inhaler further comprising an activating device for manual engagement by the patient for repeatedly metering a dose of medicament to be administered to the patient, and further comprising an advancing mechanism for advancing a counter or indexing means each time the activating device has been engaged by the patient so that a dose of medicament has been released for administration to the patient, wherein the counter or indexing means comprises an index, the index being detectable by a detection means of the inhaler, and the detection means being coupled to a locking mechanism, the locking mechanism blocking the activating device and/or any transportation mechanism of the inhaler delayed by a predetermined number of metering cycles since detection of the index.

The arrangement according to the invention allows to lockout further use of the inhaler after removal of a number of doses from the reservoir space, or an approximate number of doses left in the reservoir space with a simple, inexpensive, and reliable mechanism, so that an improved security for the patient using the inhaler can be obtained. The invention prevents the patient from trying to dose from an empty reservoir space, causing an inappropriate lack of required medicine. For certain diseases, such kind of inadvertent underdosing may cause a risk of life for the patient. Further, the manufacturer responsible for filling of the inhaling device is able to limit the number of inhalation cycles from a single reservoir space independent from the exact filing state so that even under an undesired variation of the filling level caused by the manufacturing procedure the patient can rely on the fact that each time he is able to initiate a dosing cycle, he will get an appropriate dose of medicament as required. Further the configuration according to the invention allows that manufacturer to arrange the inhaler such that the patient will not be surprised by the activation of the locking state.

In a specifically preferred embodiment of the invention the predetermined number of metering cycles since detection of the index is one. This allows the patient to obtain one further dose of medicament after the counter or indexing means indicates an empty reservoir space, providing enough time for the patient even under acute symptoms to obtain a freshly filled inhaler or cartridge, without the need to carry-along a second inhaler all the time as a replacement. Further, the patient will not be surprised by the activation of the locking state. Moreover, there is no need to provide a larger number of doses by the manufacturer in excess of the nominal number to avoid disposal of valuable medicament powder.

In a preferred embodiment the inhaler comprises a reservoir space for a large number of doses of pharmaceutical powder medicament, the activating device for manual engagement by the patient being connected to a transportation mechanism for moving a metering means at least from a filling position for receiving a dose of medicament powder from the reservoir space into an emptying position for releasing said dose of medicament powder into an air duct, for repeatedly metering a dose of medicament to be administered to the patient, and further the advancing mechanism being connected to the transportation mechanism for advancing the counter or indexing means each time the transportation mechanism moved the metering means so that a dose of medicament has been released for administration to a patient, wherein the locking mechanism blocks the activating device and/or the transportation mechanism after the predetermined number of metering cycles since detection of the index.

In a particularly preferred embodiment of the invention the inhaler comprises a receptacle for a pharmaceutical powder cartridge comprising a reservoir space for a large number of doses of pharmaceutical powder medicament. Thus, the inhaler may be used several times and a replaceable cartridge can be used to minimize the costs of the medical treatment and the amount of waste generated. Additionally, use of a single inhaler type is possible for a variety of medicaments provided in different cartridges, thus improving the over all economic effect of such an inhaler.

The invention can be easily set into practice if the index is formed by a signaling section of a mechanical counter or indexing means. In a most simple and cost effective manner the signaling section is formed by a notch or cam, so that the index can be detected mechanically. Consequently, in a further preferred embodiment of the invention, the detection means comprises a signaling lever for biased engagement with the signaling section of the counter or indexing means.

In a preferred embodiment of the invention enabling realization of delayed activation of the blocking of the activating device and/or the transportation mechanism the signaling lever is in hinged connection with a rest lever such that a movement of the signaling lever is transmitted to the rest lever, the rest lever comprising a pilot section allowing the rest lever being biased against the activating device and/or the transportation mechanism, and the rest lever being in positive engagement with the activating device and/or the transportation mechanism by means of a hook/notch arrangement, after the transportation mechanism reaches the emptying position for releasing a dose of medicament powder, and thus arresting the activating device and/or the transportation mechanism so that no further dosing cycle can be performed.

The blocked state of the inhaler is easily recognizable for the user if the activating device is arrested in a position different from normal operation position to unambiguously indicate the blocking state of the inhaler.

For repeated use of the inhaler with replaceable cartridges it is preferred if the position of the signaling lever and the rest lever is reset to normal operating position, releasing the activating device and/or the transportation from the blocked state, on insertion of a fresh unused pharmaceutical powder cartridge.

Where required, for instance by the specific properties of the medicament applied, the inhaler may be used as a one way device if the receptacle for a pharmaceutical powder cartridge comprising a pharmaceutical powder cartridge is closed by a lid of the non-removable snap on type.

The objects of the invention are further obtained by a pharmaceutical powder cartridge for use with an inhaler as described above, comprising at least one reservoir space for receiving a large number of doses of pharmaceutical powder medicament, having a dose counter or indexing ring carrying a multiplicity of numbers or graphical or colored visual information for a user, which ring is movable relative to a cartridge body by an advancing mechanism of the inhaler, the counter or indexing ring comprising a signaling section for activating a locking mechanism of the inhaler once the counter or indexing ring reaches a predetermined position relative to the cartridge body.

In a most simple and cost effective manner the signaling section is formed by a notch or cam for activating a signaling lever of the inhaler, thus allowing simple and reliable mechanical detection of the signaling section.

To improve the security and reliability of a pharmaceutical powder cartridge according to the invention, the dose counter or indexing means comprises a securing means preventing the counter or indexing ring from unintended rotation with respect to the cartridge body by applying a frictional force, or a notch/cam type security arrangement.

For simple and reliable mechanical detection of the signaling section a pharmaceutical powder cartridge according to the invention further comprises an opening for engagement of a signaling lever of a locking mechanism of the inhaler with the counter or indexing ring.

Further improved security of a pharmaceutical powder cartridge according to the invention can be obtained by a ratchet mechanism provided in the cartridge body interacting with a toothed section of the counter or indexing ring preventing the counter or indexing ring from being reversed even by user manipulation, probably even when using light tools, like a small screwdriver, a pen, or the like.

Misuse of an empty pharmaceutical powder cartridge according to the invention can be most prevented if the counter or indexing ring further comprises a notch or hook for forced engagement with a corresponding hook or notch within the cartridge body once the counter or indexing ring reaches a position indicating that the predetermined number of medicament doses have been removed, preventing any further movement of the counter or indexing ring in either direction, once engaged.

In a further preferred embodiment of a pharmaceutical powder cartridge according to the invention the pharmaceutical powder cartridge further comprising a lid, the lid covering an opening of the at least one reservoir space for receiving a large number of doses of pharmaceutical powder medicament, and a groove surrounding said opening containing the dose counter or indexing ring, wherein the lid and the interior edge of the opening comprise each a collar to provide a tight snap-on fastening of the lid, so that the at least one reservoir space is sufficiently sealed against the environment and the counter or indexing ring cannot be removed without destroying the cartridge.

The invention can be used most effectively by use of an inhaler according to the invention together with a pharmaceutical powder cartridge according to the invention.

The object and advantages of the invention are further obtained by a method for operating an inhaler for powdered medicaments, comprising the steps of releasing a medicament dose from a reservoir space, on engagement of an activating device of the inhaler by a patient, advancing a counter or indexing means comprising an index, displaying the counter or indexing means to the patient or user of the inhaler, detecting whether the index of the counter or indexing means reached a predetermined position indicating an "empty" state of the inhaler, and on detection of the index at the predetermined position indicating an "empty" state of the inhaler, blocking the activating device and/or any transportation means after a predetermined number of additional releasing steps since detection of the "empty" state, particularly, if the number of additional releasing steps is 1 to 6, preferably one.

APPLICATION OF THE INVENTION

With the inhaler an pharmaceutical powder cartridge according to the invention, it is possible to make securely available pharmacodynamically active substances in the form of powdered pharmaceuticals even under critical conditions for the life of a patient, without making additional demands on the patient or medical carer, compared with a conventional inhalation of an individual pharmaceutical powder, and without additional handling requirements.

The inhaler and powder cartridge of the invention are particularly useful for the application of pharmaceutical powder medicaments comprising, for example, from the group of beta-sympathomimetics: salbutamol, reproterol, fenoterol, formoterol, salmeterol. Possible examples from the group of corticosteroids are: budesonide, beclomethasone, fluticasone, triamcinolone, loteprednol, mometasone, flunisolide, ciclosonide. Possible examples from the group of anticholinergics are: ipatropium bromide, thiotropium bromide, glycopyrrolate, R,R-glycopyrrolate. Possible examples from the group of analgesics and anti-migraines are: morphine, tramadol, flupirtine, sumatryptan. The following can be used from the group of peptides and proteins: cetrorelix, insulin, calcitonin, parathyroid hormone, factor VIII analogs, interferon alpha, interferon beta, heparin, FSH (follicle-stimulating hormone), colistin, tobramycin.

Pharmaceutical powder formulations which can expediently be used with the inhaler and the pharmaceutical powder cartridge according to the invention can contain various active substances, such as, for example, analgesics, anti-allergics, antibiotics, anticholinergics, antihistamines, anti-inflammatory substances, antipyretics, corticoids, steroids, antitussives, bronchodilators, diuretics, enzymes, cardiovascular agents, hormones, proteins and peptides. Examples of analgesics are codeine, diamorphine, dihydromorphine, ergotamine, fentanyl and morphine; examples of anti-allergics are cromoglycinic acid and nedocromil; examples of antibiotics are cephalosporins, fusafungine, neomycin, penicillins, pentamidine, streptomycin, sulphonamides and tetracyclines, colistin, tobramycin, examples of anticholinergics are atropine, atropine methonitrate, ipratropium bromide, oxitropium bromide, trospium chloride and thiotropium bromide; examples of antihistamines are azelastine, flezelastine and methapyrilene; examples of anti-inflammatory substances are beclomethasone, budesonide, loteprednol, dexamethasone, flunisolide, fluticasone, tipredane, triamcinolone, mometasone; examples of antitussives are narcotine and noscapine; examples of bronchodilators are bambuterol, bitolterol, carbuterol, clenbuterol, ephedrine, epinephrine, formoterol, fenoterol, hexoprenaline, ibuterol, isoprenaline, isoprotenerol, metaprotenerol, orciprenaline, phenylephrine, phenylpropanolamine, pirbuterol, procaterol, reproterol, rimiterol, salbutamol, salmeterol, sulfonterol, terbutaline and tolobuterol; examples of diuretics are amiloride and furosemide; an example of an enzyme is trypsin; examples of cardiovascular agents are diltiazem and nitroglycerin; examples of hormones are cortisone, hydrocortisone and prednisolone; examples of proteins and peptides are cyclosporine, cetrorelix, glucagon and insulin. Further active substances which can be used are adrenochrome, colchicine, heparin, scopolamine. The active substances listed by way of example can be used as free bases or acids or as pharmaceutically acceptable salts. Counterions which can be used include, for example, physiological alkaline earth metals or alkali metals or amines, for example acetate, benzene sulphonate, benzoate, hydrogen carbonate, hydrogen tartrate, bromide, chloride, iodide, carbonate, citrate, fumarate, malate, maleate, cluconate, lactate, pamoate and sulphate. Esters can also be used, for example acetate, acetonide, propionate, diproprionate, valerate.

BRIEF DESCRIPTION OF THE DRAWINGS

In the following, the invention is described by means of an non-limiting exemplary embodiment of an inhaler and a pharmaceutical powder cartridge according to the invention illustrated in the accompanying drawings, wherein.

DESCRIPTION OF A PREFERRED ILLUSTRATIVE EMBODIMENT

Generally, the design of the inhaler and the cartridge of the invention as described here as a preferred illustrative example of an embodiment correspond to the general design and working principle as described in EP 0 837 710 B1, U.S. Pat. No. 5,840,279 A, and U.S. Pat. No. 6,071,498 A, the disclosure of which is hereby incorporated by reference.

The inhaler 1 shown in the drawings 1 to 5, and 16 to 17 is an inhaler for powdered medicaments, for providing a large number of doses of pharmaceutical powder medicament from a reservoir space 2. The reservoir space 2 is provided within an exchangeable pharmaceutical powder cartridge 3, comprising the at least one reservoir space 2 for receiving a large number of doses of pharmaceutical powder. Typically, the nominal number of medicament doses provided is 200 or above per cartridge 3. The pharmaceutical powder cartridge 3 is inserted into a corresponding receptacle 30 within the inhaler 1. The receptacle 30 and, thus, the powder cartridge 3 is covered by a lid 29 as shown in FIG. 6. The lid 29 can be a conventional one which is removable by the patient to exchange the powder cartridge 3 against a fresh one, or can be of the non-removable snap on type, if for specific reasons a reuse of the inhaler with a further cartridge need to be prevented. This may be the case for medicaments specifically sensitive to dust, humidity or remainders of medicaments from previously used medicament powder.

Figure 1:
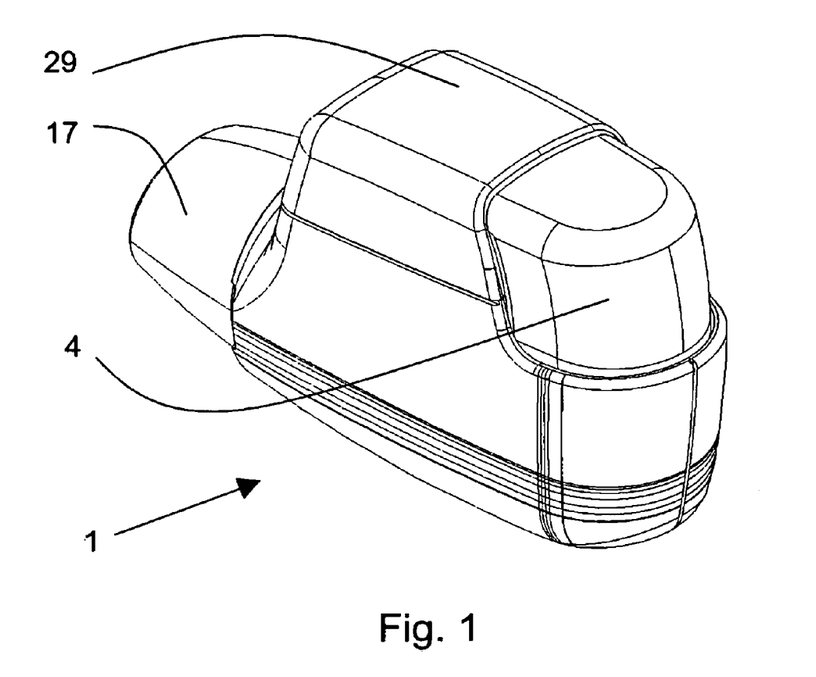
FIG. 1 shows an inhaler according to the invention in normal operating state, in a perspective view.
Figure 2:
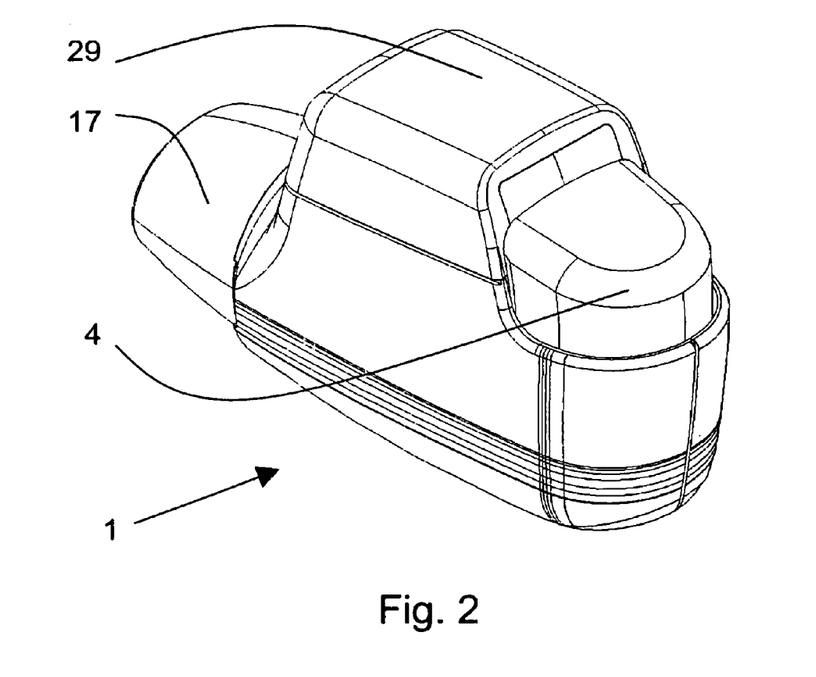
FIG. 2 shows an inhaler according to the invention in blocked operating state, in a perspective view.
Figure 3:
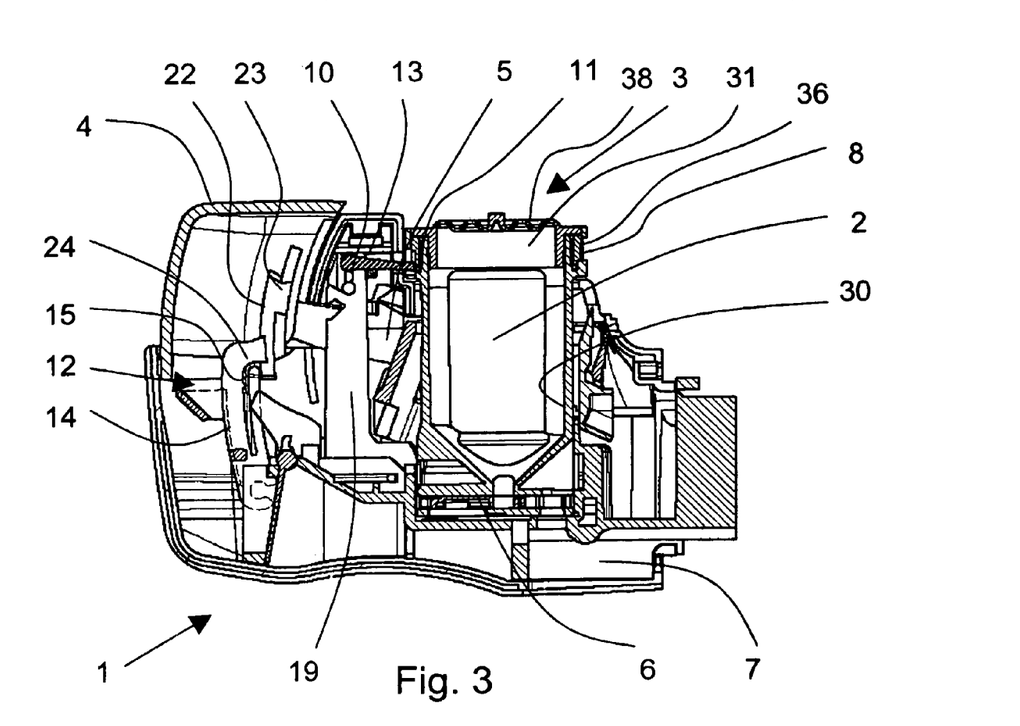
FIG. 3 shows a cross sectional view through an inhaler with inserted pharmaceutical powder cartridge according to the invention, in normal operating state, without mouthpiece and airway elements downstream of the dosing means.

The powder medicament can be received by a patient by means of an air stream. Therefore, the inhaler further comprises an activating device for manual engagement by the patient in the form of a key 4 being connected to a transportation mechanism 5 (not shown in detail) for a metering means 6 of the powder cartridge 3 at least from a filling position for receiving a dose of medicament powder from the reservoir space 2 as shown in FIG. 3 into an emptying position for releasing said dose of medicament powder into an air duct 7. From the air duct 7 the patient can inhale the medicament powder through a mouthpiece 16 (see FIG. 16) via an air stream generated by the patient. If not in use, the mouthpiece is suitably protected from dirt by a removable cover 17 as shown in FIGS. 1 and 2.

Pressing the key 4 for dosing and inhaling of the medicament need not to be coordinated by the patient. Security means inside the inhaler, as for instance described in EP 0 837 710 B1, U.S. Pat. No. 5,840,279 A, and U.S. Pat. No. 6,071,498 A prevent repeated dosing of medicament without inhaling the previous dose from the inhaler, thus preventing intended or unintentional overdosing. The key 4 and transportation mechanism 5 allow for repeatedly metering a dose of medicament to be administered to the patient, one after another.

Figure 17:
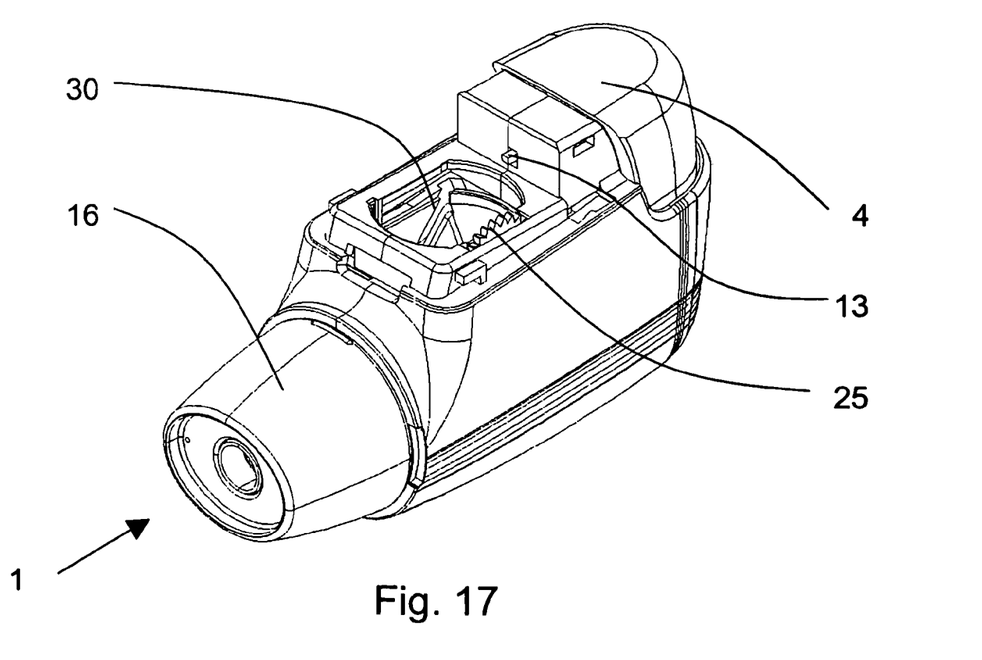
FIG. 17 shows an inhaler similar to FIG. 14 with the lid and cartridge removed.

The inhaler 1 further comprises an advancing mechanism 25 shown in FIG. 17 connected to the transportation mechanism 5 for advancing a counter or indexing means 8 each time the transportation mechanism 5 moved the metering means 6 so that a dose of medicament has been released for administration to a patient. The counter or indexing means preferably in the form of a ring 8 and contained inside the cartridge 3 comprises an index 9, the index 9 being detectable by a detection means 10 of the inhaler. The index 9 is formed by a by a notch 11 as a signaling section of a mechanical counter or indexing means 8, as can be seen from FIG. 14.

Figure 16:
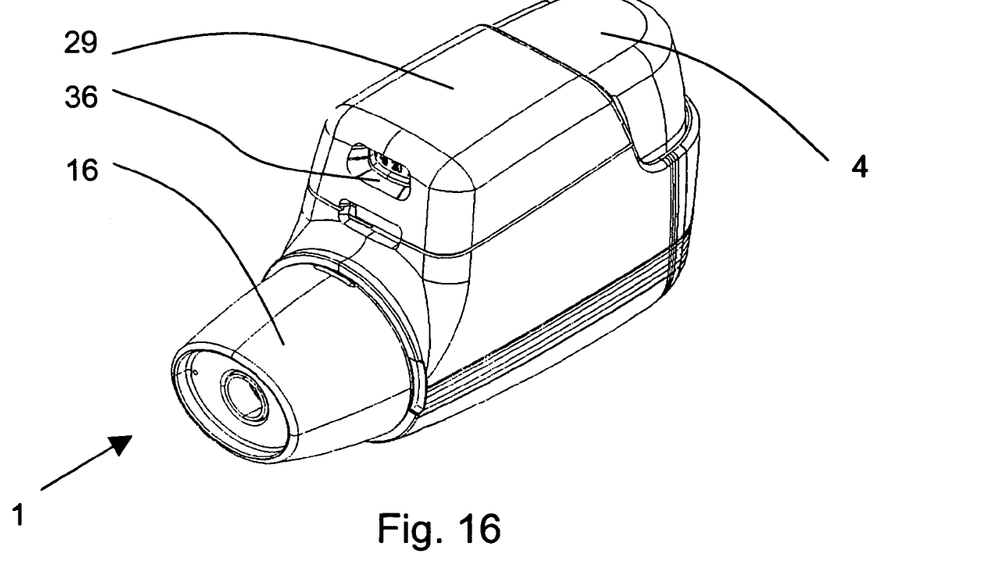
FIG. 16 shows an inhaler according to the invention in normal operating state, in a perspective front view, the protective cover of the mouthpiece removed.

The detection means 10 of the inhaler 1 is coupled to a locking mechanism 12. The locking mechanism 12 of the embodiment shown comprises the rest lever 14 with pilot section 15 and hook elements 24, and the ramp elements 22 and notch 23 interior of the key 4. The locking mechanism 12 will block the activating device/key 4 and/or the transportation mechanism 5 after a predetermined number of metering cycles since detection of the index 9. With the embodiment shown, the predetermined number of metering cycles since detection of the index 9 is one. This means that once the patient can read from the counter or indexing means 8 on the front of the inhaler 1 as shown in FIG. 16 that the predetermined number of doses have been removed from the reservoir space 2, and thus, the reservoir space 2 of the powder cartridge 3 is considered "empty", the patient has one further opportunity to activate the provision of one further dose of medicament by pressing the key 4 one further time, before the inhaler 1 will be locked. The locked state of the inhaler is shown in FIGS. 2 and 5.

Figure 8:
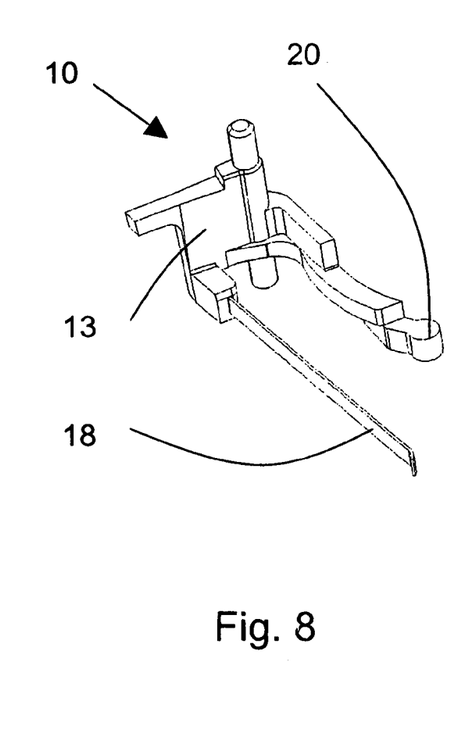
FIGS. 8 and 9 show perspective views of a signaling lever of an inhaler according to the invention.
Figure 9:
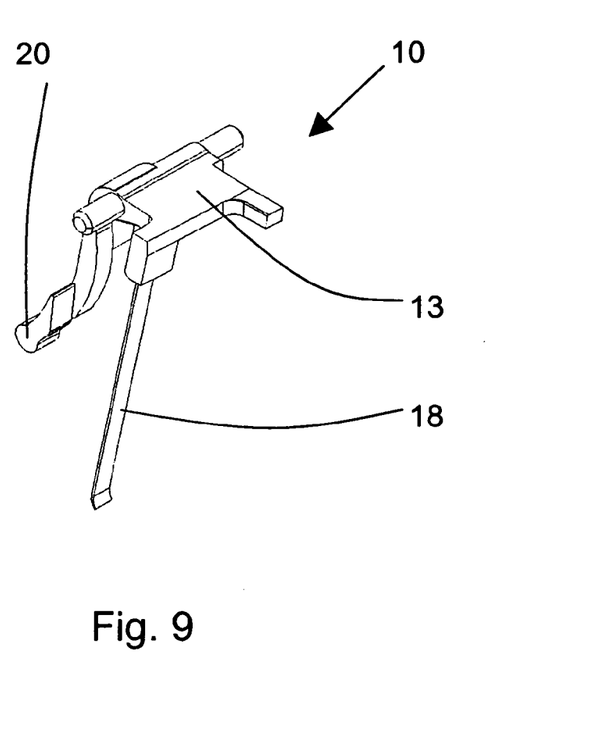
Figures 10, 11:
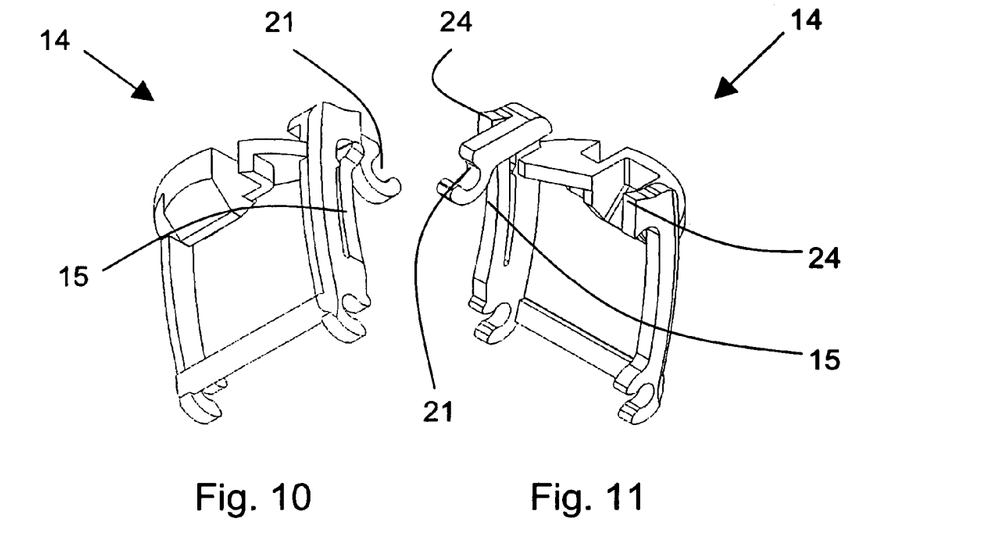
FIGS. 10 and 11 show perspective views of a rest lever of an inhaler according to the invention.

This is achieved by the signaling lever 13 of the detection means 10 of the inhaler 1. The signaling lever 13 shown in FIGS. 8 and 9 comprises a spring element 18 for biased engagement with the counter or indexing means 8, that is the signaling lever 13 is forced by spring load against the ring 8 forming the counter or indexing means of the cartridge 3. The signaling lever 13 is pivotally supported in a base frame element 19 of the inhaler 1 and in hinged connection with a rest lever 14 which in turn is also pivotally supported by the base frame element 19, as can be seen from FIGS. 3 to 5. The rest lever 14 is shown in detail in FIGS. 10 and 11. The spring element 18 of the signaling lever 13 also rests on the base frame element 19 of the inhaler 1. The hinged connection between the signaling lever 13 and the rest lever 14 is provided by a protrusion 20 of the signaling lever 13 which engages a generally unshaped receptacle 21 of the rest lever 14 such that a movement of the signaling lever 13 is transmitted to the rest lever 14.

Figure 7:
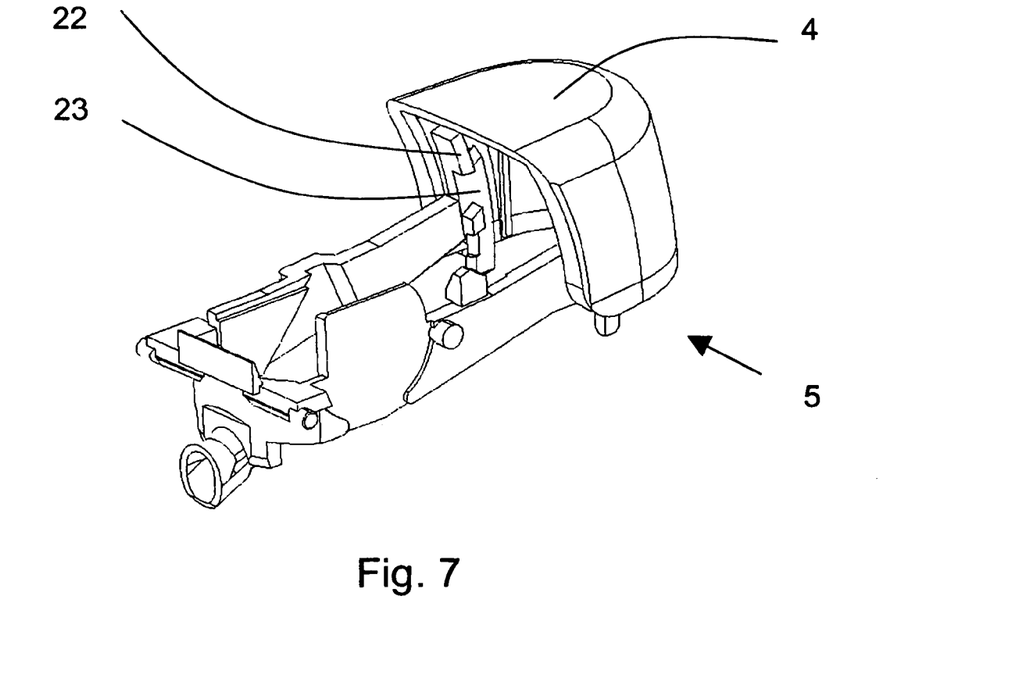
FIG. 7 shows a perspective view of an actuating device including a key according to the invention.
Figure 14:
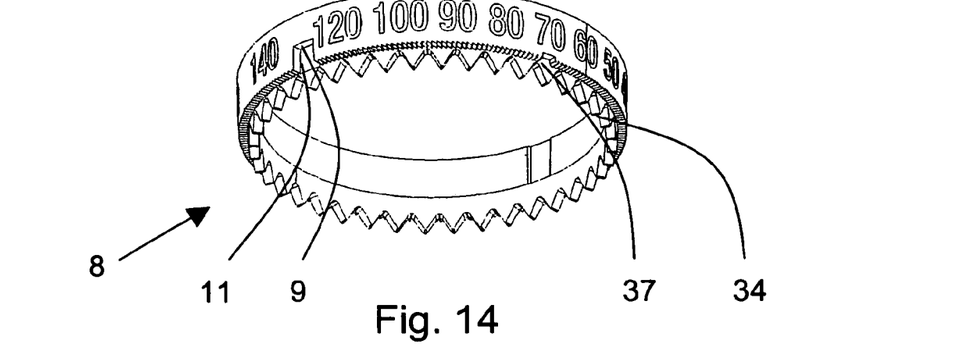
FIG. 14 shows a perspective view of a counter or indexing ring of a pharmaceutical powder cartridge according to the invention.
Figure 15:
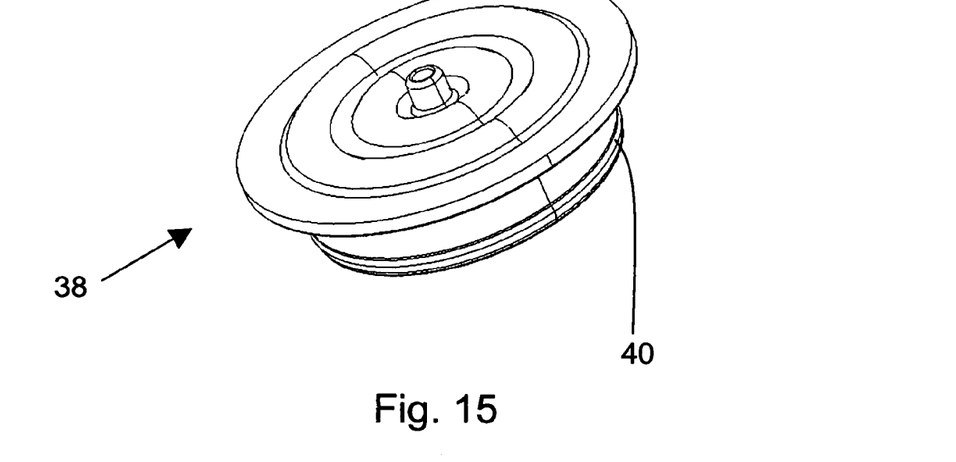
FIG. 15 shows a lid for covering an opening of the reservoir space of a pharmaceutical powder cartridge according to the invention.

If the notch 11 of the ring 8 forming the counter or indexing means as shown in FIG. 14 comes in alignment with the signaling lever 13, the signaling lever 13 is forced by its spring element 18 to swing into engagement with the notch 11, thus transmitting the movement to the rest lever 14. The rest lever 14 comprises a pilot section 15 allowing the rest lever 14 to be biased against the activating device (key 4) and/or the transportation mechanism 5 on engagement by the spring loaded signaling lever 13. The key 4 as shown in FIG. 7 in its interior comprises a ramp element 22 and, preferably on both sides, a notch 23. If now the key 4 is depressed for a further dosing action the pilot section 15 of the rest lever 14 moves along the ramp element 22 of the key 4 until it reaches an end of the ramp section 22 when the key 4 is fully depressed (see FIG. 4), releasing two hook elements 24 of the rest lever 14 for biased engagement with the key 4. When the key 4 is fully depressed, the transportation mechanism 5 reaches the emptying position of the dosing means 6 for releasing a dose of medicament powder. When the patient subsequently releases the key 4 towards its normal position, the hooks 24 come in positive engagement with the notches 23 of the key 4 preferably half-way up of the key 4, thus arresting the key 4 as the activating device and the transportation mechanism 5 for the dosing means 6 so that no further dosing cycle can be performed, as shown in FIG. 5.

Figure 4:
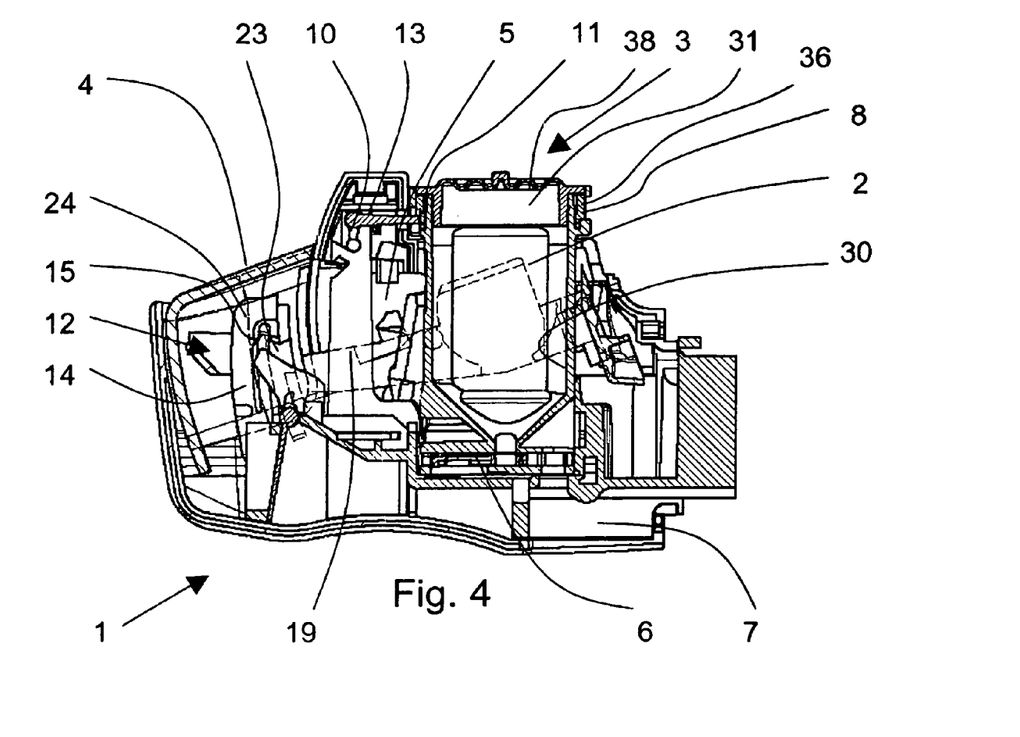
FIG. 4 shows a similar cross sectional view through an inhaler with inserted pharmaceutical powder cartridge according to the invention, in actuated operating state for releasing a medicament dose, without mouthpiece.
Figure 5:
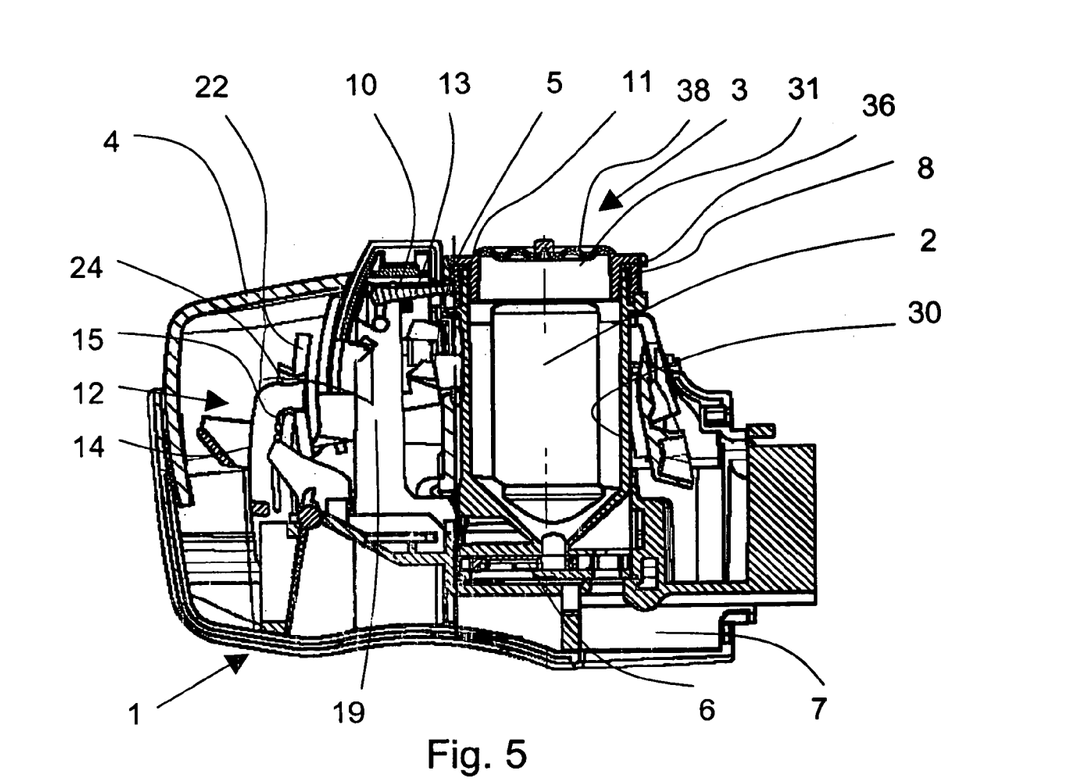
FIG. 5 shows a similar cross sectional view through an inhaler with inserted pharmaceutical powder cartridge according to the invention, in blocked operating state, without mouthpiece.
Figure 6:
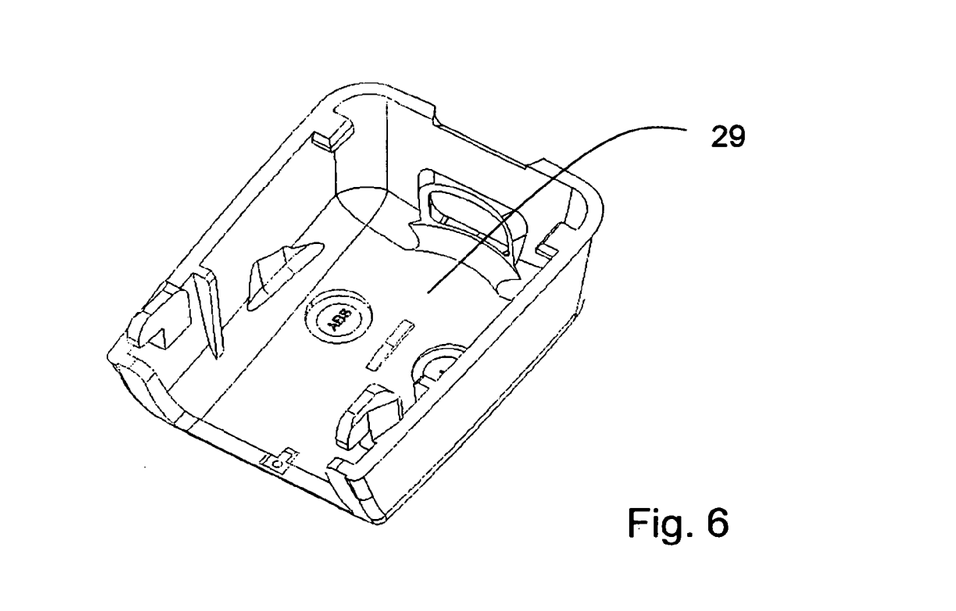
FIG. 6 shows a perspective view of the underside of a lid for a cartridge receptacle of an inhaler according to the invention.

The activating device is arrested in a position different from normal operation position as shown in FIGS. 2 and 5, thereby unambiguously indicating the blocking state of the inhaler to the patient, preferably such that the key 4 remains approximately half-way between its normal rest position as shown in FIG. 1, and a fully depressed position during an activation cycle performed by the patient as shown in FIG. 4.

For multiple use of the inhaler 1 the position of the signaling lever 13 and the rest lever 14 is reset to normal operating position, releasing the key 4 and the transportation mechanism 5 from the blocked state, on insertion of a fresh unused pharmaceutical powder cartridge.

Figures 12, 13:
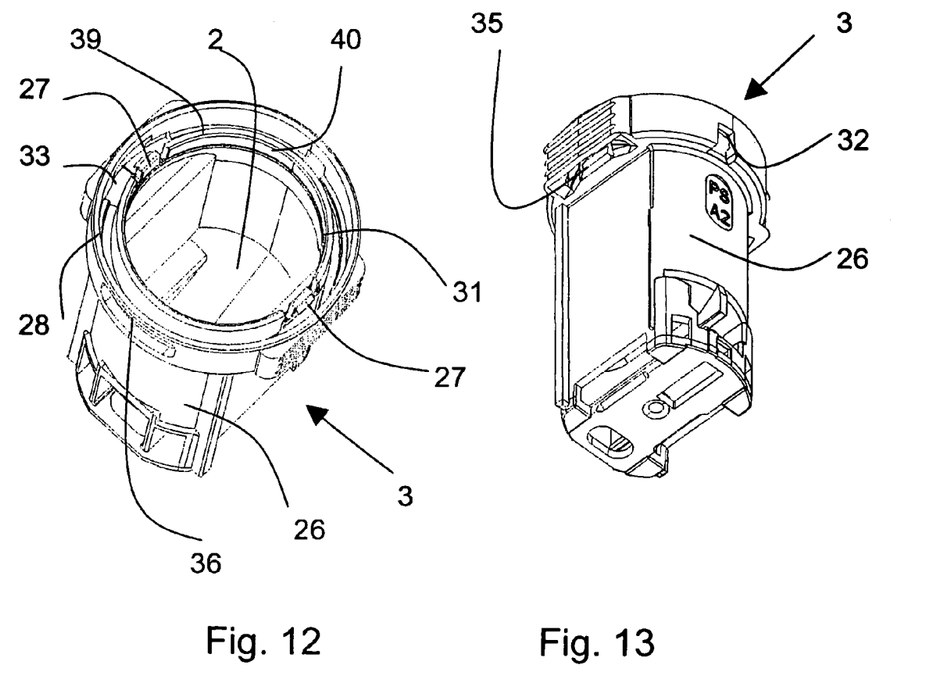
FIGS. 12 and 13 show perspective views of a body of a pharmaceutical powder cartridge of the invention.

The pharmaceutical powder cartridge 3 shown in FIGS. 12 and 13 for use with the inhaler 1 according to the embodiment described comprises a reservoir space 2 for receiving a large number of doses of pharmaceutical powder medicament, for the embodiment shown for a nominal number of 200 doses. The reservoir space 2 may be factory filled with medicament powder through a top opening 31 within the cartridge body 26.

Figure 18:
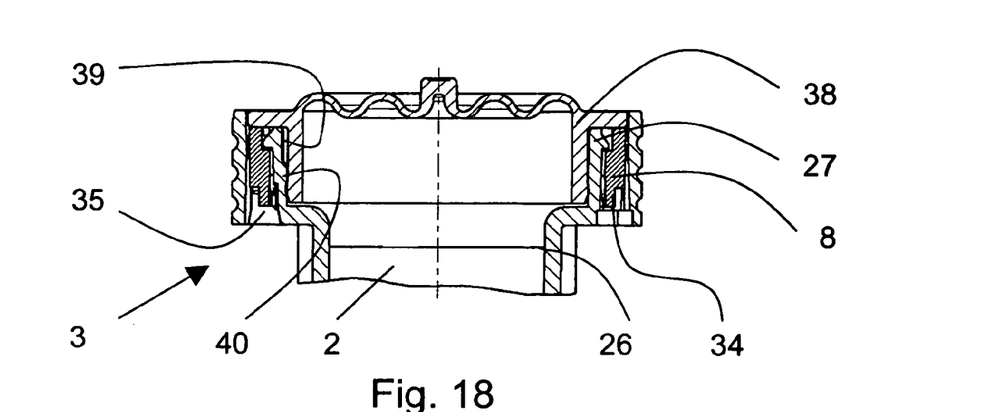
FIG. 18 shows a cross-sectional view of the top part arrangement of a pharmaceutical powder cartridge according to the invention.
Figure 19:
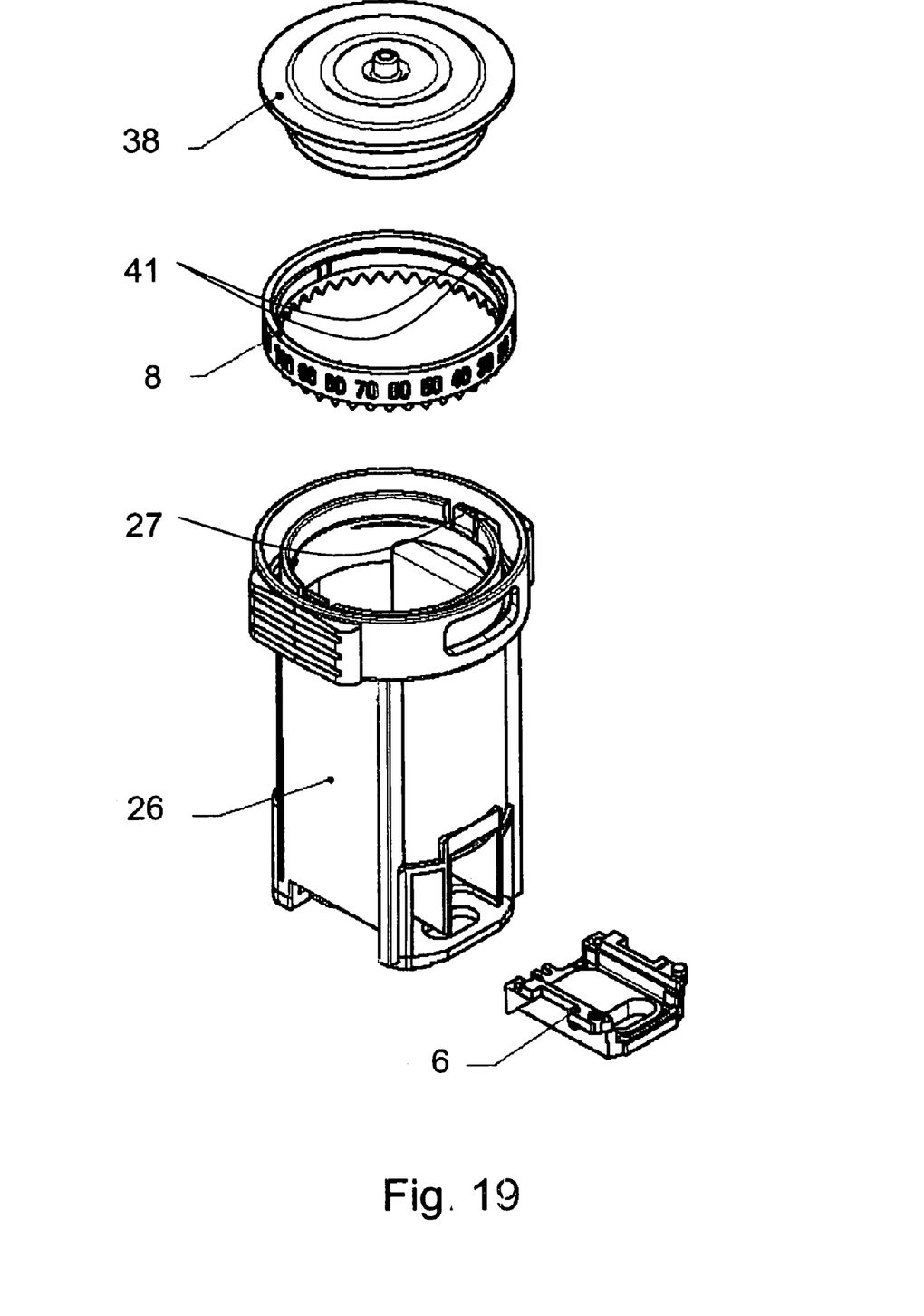
FIG. 19 shows an exploded view of a pharmaceutical powder cartridge according to the invention.

The pharmaceutical powder cartridge 3 comprises a groove 28 within the top section of its cartridge body 26 surrounding the opening 31 containing the dose counter or indexing ring 8. The ring 8 is movable relative to a cartridge body 26 by an advancing mechanism 25 of the inhaler 1. The advancing mechanism in the form of a pinion gear 25 engages with the ring 8 through opening 35 in the cartridge body 26, once the cartridge is inserted into the receptacle 30 of the inhaler 1. In the groove 28 preferably two resilient hook members 27 are located preventing the counter or indexing ring 8 from unintended rotation with respect to the cartridge body 26 by applying a frictional force. At the same time the hook members 27 prevent the ring 8 from being urged upwards by the bias force of the signaling lever 13 of the inhaler 1 once inserted into the receptacle 30 of the inhaler 1. The hook members 27 also serve to keep the ring 8 in place and rotational position during the manufacturing and filling process of the cartridge prior to fixing the lid 38 on the cartridge body 26, as shown in FIGS. 18 and 19. The cartridge body 26 further comprises an opening 32 for engagement of the signaling lever 13 of the inhaler 1 with the counter or indexing ring 8. The ring 8 can be read by the user through a viewing window 36 located in the top region of the cartridge body 26.

Inside the groove 28 there is preferably a ratchet mechanism provided by an elastically supported hook lever 33 in the cartridge body 26 interacting with a toothed section 34 of the counter or indexing ring 8 preventing the counter or indexing ring 8 from being reversed even by user manipulation, for instance by using a small screwdriver through an opening 35 for receiving the advancing mechanism 25 of the inhaler 1. The pharmaceutical powder cartridge 3 may comprise within the counter or indexing ring 8 a notch 37 or hook for forced engagement with a corresponding hook 33 or notch within the cartridge body 26 once the counter or indexing ring 8 reaches a position indicating that the predetermined number of medicament doses have been removed, preventing any further movement of the counter or indexing ring 8 in either direction, once engaged.

The counter or indexing ring 8 carries a multiplicity of numbers or, alternatively or additionally, graphical or colored visual information for a user on its outer circumference. The counter or indexing ring 8 shown in FIG. 14 comprises a signaling section for activating the locking mechanism of the inhaler 1 once the counter or indexing ring 8 reaches a predetermined position relative to the cartridge body 26, that is after 200 doses have been taken from the cartridge 3. The signaling section is formed by a notch 11 adapted for receiving the signaling lever 13 of the inhaler 1. The interior circumference of the counter or indexing ring 8 further carries two small protrusions 41 forming a notch between them, which notch is releasably engaged by one of the hook members 27 when the ring 8 is inserted into the cartridge body 26 in an orientation providing an indication through viewing window 36 associated with a full cartridge. This notch/cam security arrangement serves to keep the appropriate orientation of the ring 8 even under rough handling or shipping conditions prior to providing the full cartridge 3 to a patient as the end user.

The powder cartridge 3 further comprises a lid 38 covering the opening 31 of the reservoir space 2 and the groove 28 containing the ring 8. The lid 31 and the interior edge 39 of the opening 31 comprise each a collar 40 to provide a tight snap-on fastening for the lid 38, so that the reservoir space 2 is sufficiently sealed against the environment and the counter or indexing ring 8 cannot be removed without destroying the cartridge.

As it is evident for a skilled person, various alterations can be made with respect to the exemplary embodiment described without departing from the scope of the invention as defined in the claims.

The invention claimed is:

1. An inhaler (1) for powdered medicaments, for providing a large number of doses of pharmaceutical powder of medicament from a single reservoir space (2) or a multiplicity of reservoir spaces, which medicament can be received by a patient by means of an air stream, the inhaler further comprising an activating device (4) for manual engagement by the patient for repeatedly metering a dose of medicament to be administered to the patient, and further comprising an advancing mechanism (25) for advancing a counter or indexing means (8) each time the activating device (4) has been engaged by the patient so that a dose of medicament has been released for administration to the patient, wherein the counter or indexing means (8) comprises an index (9), the index (9) being detectable by a detection means (10) of the inhaler, and the detection means (10) being coupled to a locking mechanism (12), the locking mechanism (12) blocking the activating device (4) and/or any transportation mechanism (5) of the inhaler (1) delayed by a predetermined number of metering cycles since detection of the index (9), wherein the predetermined number of metering cycles since detection of the index (9) is at least one and wherein the activating device (4) is arrested in a position different from normal operation position to unambiguously indicate the blocking state of the inhaler.

2. The inhaler of claim 1, comprising a reservoir space (2) for a large number of doses of pharmaceutical powder medicament, the activating device (4) for manual engagement by the patient being connected to a transportation mechanism (5) for moving a metering means at least from a filling position for receiving a dose of medicament powder from the reservoir space (2) into an emptying position for releasing said dose of medicament powder into an air duct (7), for repeatedly metering a dose of medicament to be administered to the patient, and further the advancing mechanism (25) being connected to the transportation mechanism (5) for advancing the counter or indexing means (8) each time the transportation mechanism (5) moved the metering means so that a dose of medicament has been released for administration to a patient, wherein the locking mechanism (12) blocks the activating device (4) and/or the transportation mechanism (5) after the predetermined number of metering cycles since detection of the index (9).

3. The inhaler of claim 1, wherein the inhaler (1) comprises a receptacle (30) for a pharmaceutical powder cartridge (3) comprising a reservoir space (2) for a large number of doses of pharmaceutical powder medicament.

4. The inhaler of claim 3, wherein the receptacle (30) for a pharmaceutical powder cartridge comprising a pharmaceutical powder cartridge (3) is closed by a lid (29) of the non-removable snap on type.

5. The inhaler of claim 1, wherein the index (9) is formed by a signaling section of a mechanical counter or indexing means (8).

6. The inhaler of claim 5, wherein the signaling section (9) is formed by a notch or cam (38).

7. The inhaler of claim 6, wherein the detection means (10) comprises a signaling lever (13) for biased engagement with the signaling section of the counter or indexing means (8).

8. The inhaler of claim 1, further comprising a pharmaceutical powder cartridge that includes at least one reservoir space (2) for receiving a large number of doses of pharmaceutical powder medicament, having a dose counter or indexing ring (8) carrying a multiplicity of numbers or graphical or colored visual information for a user, which ring (8) is movable relative to a cartridge body (26) by an advancing mechanism (25) of the inhaler (1), the counter or indexing ring (8) comprising a signaling section (9) for activating a locking mechanism (12) of the inhaler (1) once the counter or indexing ring (8) reaches a predetermined position relative to the cartridge body (26),
wherein the inhaler is operationally linked with the pharmaceutical powder cartridge, and activating the inhaler delivers a dose of said medicament to the patient.

9. Pharmaceutical powder cartridge according to claim 8, wherein the signaling section (9) is formed by a notch or cam (11) for activating a signaling lever of the inhaler.

10. Pharmaceutical powder cartridge according to claim 8, wherein the dose counter or indexing means (8) comprises a securing means (27) preventing the counter or indexing ring (8) from unintended rotation with respect to the cartridge body (26) by applying a frictional force, or a notch/cam type security arrangement.

11. Pharmaceutical powder cartridge according to claim 8, further comprising an opening (32) for engagement of a signaling lever (13) of a locking mechanism (12) of the inhaler (1) with the counter or indexing ring (8).

12. Pharmaceutical powder cartridge according to claim 8, wherein there is a ratchet mechanism (33) provided in the cartridge body (26) interacting with a toothed section (34) of the counter or indexing ring (8) preventing the counter or indexing ring (8) from being reversed even by user manipulation.

13. Pharmaceutical powder cartridge according to claim 8, wherein the counter or indexing ring (8) further comprises a notch or hook (37) for forced engagement with a corresponding hook or notch (33) within the cartridge body (26) once the counter or indexing ring (8) reaches a position indicating that the predetermined number of medicament doses have been removed, preventing any further movement of the counter or indexing ring (8) in either direction, once engaged.

14. An inhaler (1) for powdered medicaments, for providing a large number of doses of pharmaceutical powder of medicament from a single reservoir space (2) or a multiplicity of reservoir spaces, which medicament can be received by a patient by means of an air stream, the inhaler further comprising an activating device (4) for manual engagement by the patient for repeatedly metering a dose of medicament to be administered to the patient, and further comprising an advancing mechanism (25) for advancing a counter or indexing means (8) each time the activating device (4) has been engaged by the patient so that a dose of medicament has been released for administration to the patient, wherein the counter or indexing means (8) comprises an index (9), the index (9) being detectable by a detection means (10) of the inhaler, and the detection means (10) being coupled to a locking mechanism (12), the locking mechanism (12) blocking the activating device (4) and/or any transportation mechanism (5) of the inhaler (1) delayed by a predetermined number of metering cycles since detection of the index (9),
wherein the index (9) is formed by a signaling section of a mechanical counter or indexing means (8), the signaling section (9) is formed by a notch or cam (38), the detection means (10) comprises a signaling lever (13) for biased engagement with the signaling section of the counter or indexing means (8),
the signaling lever (13) is in hinged connection with a rest lever (14) such that a movement of the signaling lever (13) is transmitted to the rest lever (14), the rest lever (14) comprising a pilot section (15) allowing the rest lever (14) being biased against the activating device (4) and/or the transportation mechanism (5), and the rest lever (14) being in positive engagement with the activating device (4) and/or the transportation mechanism (5) by means of a hook/notch arrangement, after the transportation mechanism (5) reaches the emptying position for releasing a dose of medicament powder, and thus arresting the activating device (4) and/or the transportation mechanism (5) so that no further dosing cycle can be performed.

15. The inhaler of claim 14, wherein the activating device (4) is arrested in a position different from normal operation position to unambiguously indicate the blocking state of the inhaler.

16. The inhaler of claim 14, wherein the position of the signaling lever (13) and the rest lever (14) is reset to normal operating position, releasing the activating device (4) and/or the transportation (5) from the blocked state, on insertion of a fresh unused pharmaceutical powder cartridge (3).

17. Pharmaceutical powder cartridge for use with an inhaler (1) for powdered medicaments, for providing a large number of doses of pharmaceutical powder of medicament from a single reservoir space (2) or a multiplicity of reservoir spaces, which medicament can be received by a patient by means of an air stream, the inhaler further comprising an activating device (4) for manual engagement by the patient for repeatedly metering a dose of medicament to be administered to the patient, and further comprising an advancing mechanism (25) for advancing a counter or indexing means (8) each time the activating device (4) has been engaged by the patient so that a dose of medicament has been released for administration to the patient, wherein the counter or indexing means (8) comprises an index (9), the index (9) being detectable by a detection means (10) of the inhaler, and the detection means (10) being coupled to a locking mechanism (12), the locking mechanism (12) blocking the activating device (4) and/or any transportation mechanism (5) of the inhaler (1) delayed by a predetermined number of metering cycles since detection of the index (9), comprising at least one reservoir space (2) for receiving a large number of doses of pharmaceutical powder medicament, having a dose counter or indexing ring (8) carrying a multiplicity of numbers or graphical or colored visual information for a user, which ring (8) is movable relative to a cartridge body (26) by an advancing mechanism (25) of the inhaler (1), the counter or indexing ring (8) comprising a signaling section (9) for activating a locking mechanism (12) of the inhaler (1) once the counter or indexing ring (8) reaches a predetermined position relative to the cartridge body (26), further comprising a lid (38), the lid (38) covering an opening (31) of the at least one reservoir space (2) for receiving a large number of doses of pharmaceutical powder medicament, and a groove (28) surrounding said opening (31) containing the dose counter or indexing ring (8), wherein the lid (38) and the interior edge (39) of the opening (31) comprise each a collar (40) to provide a tight snap-on fastening of the lid (38), so that the at least one reservoir space (2) is sufficiently sealed against the environment and the counter or indexing ring (8) cannot be removed without destroying the cartridge.

\* \* \* \* \*

UNITED STATES PATENT AND TRADEMARK OFFICE
CERTIFICATE OF CORRECTION

PATENT NO. : 8,051,851 B2  
APPLICATION NO. : 11/183182  
DATED : November 8, 2011  
INVENTOR(S) : Herder et al.

Page 1 of 1

It is certified that error appears in the above-identified patent and that said Letters Patent is hereby corrected as shown below:

Title page, item (73) Assignee should read as follows:

-- Almirall, S. A., Barcelona, Spain --

Signed and Sealed this  
Ninth Day of April, 2013

Teresa Stanek Rea  
*Acting Director of the United States Patent and Trademark Office*